United States Patent
Balzer et al.

(10) Patent No.: US 9,265,966 B2
(45) Date of Patent: Feb. 23, 2016

(54) DYNAMIC MULTI-LAYER THERAPEUTIC MAGNETIC DEVICE

(71) Applicants: David Balzer, Orange, CA (US); Sungwook Moon, Seoul (KR)

(72) Inventors: David Balzer, Orange, CA (US); Sungwook Moon, Seoul (KR)

(73) Assignee: NIKKEN INTERNATIONAL, INC., Irvine, CA (US)

( * ) Notice: Subject to any disclaimer, the term of this patent is extended or adjusted under 35 U.S.C. 154(b) by 454 days.

(21) Appl. No.: 13/646,648

(22) Filed: Oct. 5, 2012

(65) Prior Publication Data
US 2014/0100410 A1    Apr. 10, 2014

(51) Int. Cl.
*A61B 17/52* (2006.01)
*A61N 2/00* (2006.01)
*A61N 2/06* (2006.01)
*A61N 1/36* (2006.01)
*A61N 1/34* (2006.01)

(52) U.S. Cl.
CPC .............. *A61N 2/06* (2013.01); *A61N 1/36014* (2013.01); *A61N 2001/34* (2013.01); *Y10T 29/49826* (2015.01)

(58) Field of Classification Search
CPC . A61N 2001/34; A61N 1/36014; A61N 2/06; Y10T 29/49826
USPC ................... 600/9–15; 128/897–899; 29/428; 48/9–15
See application file for complete search history.

(56) References Cited

U.S. PATENT DOCUMENTS

| 3,921,620 | A | | 11/1975 | Nakayama |
| 4,033,054 | A | * | 7/1977 | Fukuoka ............ 36/11.5 |
| 4,109,661 | A | * | 8/1978 | Fukuoka ............ 36/141 |
| 5,035,017 | A | | 7/1991 | Komuro |
| 5,158,526 | A | | 10/1992 | Bricot |
| 5,233,768 | A | | 8/1993 | Humphreys |
| 5,965,282 | A | | 10/1999 | Baermann |
| 6,151,807 | A | * | 11/2000 | Qui et al. ............ 36/140 |
| 6,263,592 | B1 | * | 7/2001 | Chen ................. 36/44 |

(Continued)

FOREIGN PATENT DOCUMENTS

| CN | 101485506 | 7/2009 |
| GB | 2410441 | 8/2005 |

(Continued)

OTHER PUBLICATIONS

Young, Lee W.; Transmittal of International Search Report and Written Opinion mailed on Dec. 10, 2012 in Applicant's co-pending PCT Application No. PCT/US2012/059110.

(Continued)

*Primary Examiner* — Navin Natnithithadha
*Assistant Examiner* — Sunita Reddy
(74) *Attorney, Agent, or Firm* — Cislo & Thomas, LLP

(57) ABSTRACT

A multi-layer magnetic device comprising two or more layers containing magnets or ferromagnetic material to be applied to areas of the body of a mammal in which the first layer has one or more protrusions and the second layer has one or more receiving zones that are positioned to align with the protrusions of the first layer. At least a portion of the first layer has a first magnetic pattern, and at least a portion of the second layer has a second magnetic pattern such that, when the protrusions are aligned with the receiving zones, at least one region of the first magnetic pattern faces at least one region of the second magnetic pattern of like polarity thereby repulsing one another.

13 Claims, 8 Drawing Sheets

(56) References Cited

U.S. PATENT DOCUMENTS

| | | |
|---|---|---|
| 6,267,719 B1 | 7/2001 | Grisoni et al. |
| 6,322,491 B1 * | 11/2001 | Bove et al. ............... 600/15 |
| 6,846,379 B1 | 1/2005 | Bove et al. |
| 7,216,508 B2 | 5/2007 | Kretchmer et al. |
| 2004/0060651 A1 | 4/2004 | Komatsu |
| 2004/0230139 A1 | 11/2004 | Chang |
| 2009/0216068 A1 | 8/2009 | Thomas et al. |

FOREIGN PATENT DOCUMENTS

| | | |
|---|---|---|
| JP | 2002-034606 | 2/2002 |
| JP | 2005-270542 | 10/2005 |
| JP | 2008-173309 | 7/2008 |
| JP | 2010-201143 | 9/2010 |
| WO | WO 2011/034255 | 3/2011 |

OTHER PUBLICATIONS

Copy of Office Action dated Apr. 30, 2015 issued against Mexican Patent Application No. MX/A/2013/006009.

Copy of European Search Report dated Mar. 26, 2015 issued against European Patent Application No. 12838960.8.

* cited by examiner

DYNAMIC MULTI-LAYER THERAPEUTIC MAGNETIC DEVICE

CROSS-REFERENCES TO RELATED APPLICATIONS

This patent application claims the benefit of U.S. Provisional Application No. 61/545,013, filed Oct. 7, 2011, which application is incorporated herein by this reference thereto.

BACKGROUND OF THE INVENTION

This invention relates to the field of magnetic therapy devices, and in particular to the field of consumer magnetic therapy devices that produce a multitude of magnetic flux lines at the application surface.

SUMMARY OF THE INVENTION

The invention is a multi-layer magnetic device comprising two or more layers containing magnets or ferromagnetic material to be applied to areas of the body of a mammal in which the first layer has one or more protrusions and the second layer has one or more receiving zones that are positioned to align with the protrusions of the first layer. At least a portion of the first layer has a first magnetic pattern, and at least a portion of the second layer has a second magnetic pattern such that, when the protrusions are aligned with the receiving zones, at least one region of the first magnetic pattern faces at least one region of the second magnetic pattern of like polarity thereby repulsing one another.

DESCRIPTION OF THE PREFERRED EMBODIMENTS

Figure 1:
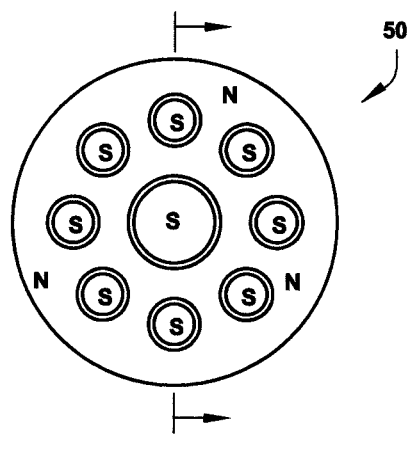
FIG. 1 is a top plan view of one embodiment of a therapeutic magnetic device in keeping with the present invention.

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

One embodiment of the present invention comprises two (2) separate and distinct layers of flexible, ferromagnetic material combined into a small planar material to be applied to areas of the body. The first layer is the "cast" layer in which a number of protrusions are formed on one side; the second layer is the "die-cut" layer having a number of holes that match the arrangement of protrusions of the cast layer. Before the layers are aligned and assembled, each layer is separately magnetized. The two layers are then assembled with either the two south poles or the two north poles facing each other. Once the layers are aligned and pressed together, the protrusions from the cast layer and the application surface of the die-cut layer form a surface magnetic pattern that has both polarities.

One of the key fabrication advantages of this approach is that the magnetization of each layer can be induced after casting or stamping but before pressing the two layers together. Another key fabrication advantage of this approach is that it is readily amenable to a virtually unlimited number of protrusion and receiving zone variations in the choice of number, size, shape, and proximity of such protrusions. Thus, a variety of flux line configurations may be produced simply by varying the number, size, and placement of the protrusions and receiving zones.

One of the key functional advantages in some embodiments of the present invention is that the forced like-pole juxtaposition of members 100 and 200 may produce magnetic fields that extend considerably deeper into the user's body. Also, the placement and configurations of the protrusions and recesses themselves can be fashioned to increase the overall depth of penetration once applied to the surface of the body. A further key functional advantage is that the repulsive forces between two layers once assembled will act to form a magnetic flux pattern that is dynamic, increasing and decreasing as the user compresses and then releases the device while in use.

For example, using this magnetic configuration in shoe insoles, as the user applies his/her weight to the insole, the weight forces the layers together, closing the air gap created by the magnetic repulsion between the two layers, thereby resulting in a fluid-type flux "pumping."

Example 1

Thus, as shown in FIGS. 1 through 7, one embodiment of the present invention involves a therapeutic magnetic device 50 for use on a human or an animal comprising a first member 100 and a second member 200. The first member 100, which may be a thin, flexible sheet material, comprises a mating surface 102 and distal surface 104. The mating surface 102 of the first member 100 comprises a number of protrusions 106.

The second member 200, which likewise may be a thin, flexible sheet material, comprises a mating surface 202 and a distal surface 204. The mating surface 202 of the second member 200 has one or more internal edges 205 that define a plurality of receiving zones 206 for aligning with the plurality of protrusions 106. The receiving zones 206 may be orifices or may be recesses, depending on the intended application and other dimensional parameters of the first and second members 100 and 200 and the desired magnetic field gradients at the application surface.

The first member 100, or at least a portion of it, is induced with a magnetic pattern 108. The second member 200, or at least a portion of it, is similarly induced with a magnetic patterns 208 such that, when the protrusions 106 are aligned with the receiving zones 206, at least a portion of the first magnetic pattern 108 faces at least a portion of the second magnetic pattern 208 in such a manner as to have like polarities facing each other thereby producing a repulsive magnetic force on one another.

The result is a therapeutically effective plurality of magnetic flux lines at an application surface 204' of the device 50, which in some embodiments, is distal surface 204 of the second member 200. It is also intended, in some embodiments, that a number of characteristics of this plurality of magnetic flux lines will vary as the distance L between the mating surface 102 of the first member 100 and mating surface 202 of the second member 200 varies.

One benefit of some embodiments of this innovation is that the magnetization processes are greatly simplified. The first member 100 with its plurality of protrusions 106 may be placed in a magnetic field of a desired magnetic pattern 108 so as to impose this magnetic pattern 108 upon the protrusion-bearing mating surface 102. The second member 200 with its plurality of receiving zones 206 may be placed in a separate magnetic field of a desired magnetic pattern 208 so as to impose this separate magnetic pattern 208 upon the mating surface 202 of the second member 200 with its receiving zones 206. Then, by mating the plurality of protrusions 106 on the first sheet with the plurality of receiving features 206 on the second sheet, portions of the two magnetic patterns 108 and 208 come into repulsive magnetic communication with one another.

Another benefit of other embodiments of the present invention is that the magnetic patterns and interactions created by the aligning layers produce at an application surface a therapeutically beneficial plurality of magnetic flux lines in multiple directions in a predetermined pattern. And, in some embodiments, this plurality of magnetic flux lines is dynamic, varying in strength, and sometimes even in direction and depth, as the layers are compressed despite the repulsive forces acting between the layers.

The first member 100 may be forced into alignment with the second member 200 but the supporting structures on either side of the first and second members 100 and 200. Although not shown in FIGS. 1 and 2, first member 100 may be supported by a larger structure, such as a casing, an insole for insertion into a shoe, or a sheet or other cloth portion of a blanket or the like (not shown in the Figures). Second member 200, likewise, may be supported by a larger structure, such as a connected portion of the casing, a second layer of an insole, or a second sheet or cloth that comprises a blanket. In such embodiments, first member 100 is forced up against the second member 200.

Once the two members 100 and 200 are aligned as discussed above and forced against one another by such larger structure, the two facing magnetic patterns repel each other forcing the first and second members 100 and 200 apart, whether greatly or only slightly. In either case, the dynamic nature of the plurality of magnetic flux lines created by these repulsive forces may be therapeutically significant at the application surface and deep within the tissues of the user.

Figure 2:
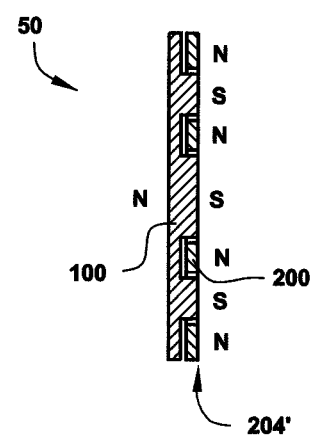
FIG. 2 is a cross-sectional view of the device of FIG. 1 taken along centerline thereof showing the protrusions 106 of the first member 100 aligned with the receiving zones 206 of the second member 200 in keeping with one embodiment of the present invention.

Alternatively, as illustrated in FIGS. 1 and 2, the first member 100 may be press fit onto the second member 200, once the two members are aligned as discussed above, or they may connected by an adhesive or the like such that first member 100 may still move relative to second member 200 but still remain connected to, or at least aligned with and in magnetic communication with, the second member 200. Further alternatively, as shown in FIG. 3, the first and second members 100 and 200 may be separated from one another by using an elastic sheet that may further facilitate or enhance the ability of first member 100 to move relative to second member 200 during use.

The protrusion/receiving zone combinations in some embodiments can act as a plurality of protruding keying features on the first sheet with a plurality of receiving keying features on the second sheet. The mating of these features then act as a key and keyhole locking in the intended orientation of the first member 100 relative to the second member 200, causing at least one region of the first magnetic pattern 108 to face at least one region of the second magnetic pattern 208 of like polarity in repelling fashion. As the distance between the first and second sheets varies, the therapeutically effective plurality of magnetic flux lines produced thereby at an application surface of the device 50 will vary.

Figure 3:
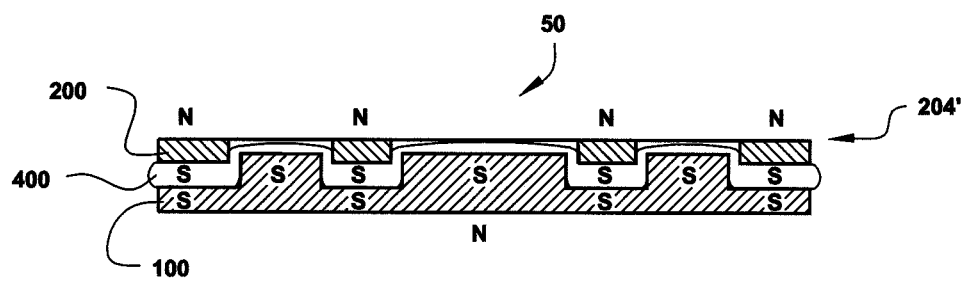
FIG. 3 is a cross-sectional view of a device similar to that of FIG. 6, except that the device additionally comprises a sheet 302 between the first and second members in keeping with another embodiment of the present invention.
Figure 4:
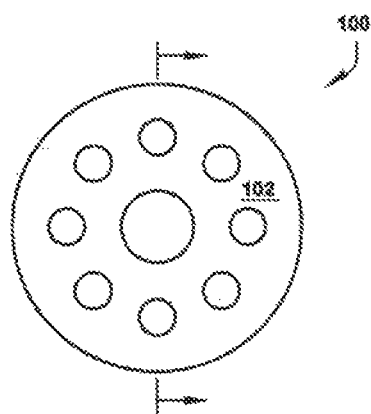
FIG. 4 is a top plan view of the first member 100 of the device of FIG. 1.
Figure 5:
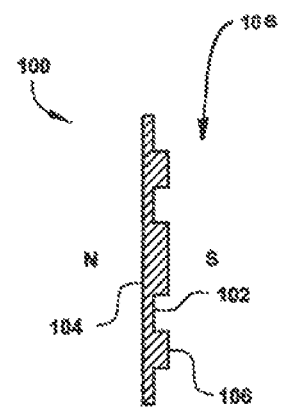
FIG. 5 is a cross-sectional view of the first member 100 of FIG. 4 taken along centerline thereof.
Figure 6:
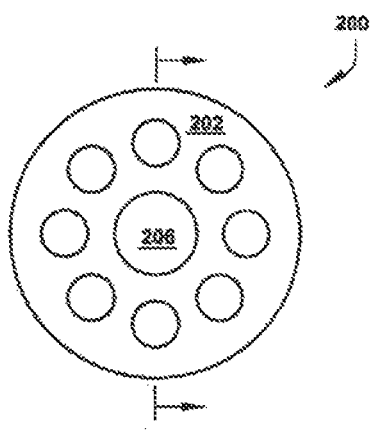
FIG. 6 is a top plan view of the second member 200 of the device of FIG. 1.
Figure 7:
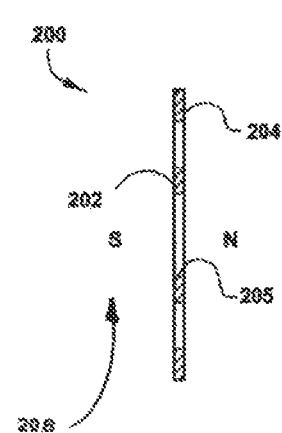
FIG. 7 is a cross-sectional view of the second member 200 of FIG. 6 taken along centerline thereof.
Figure 8:
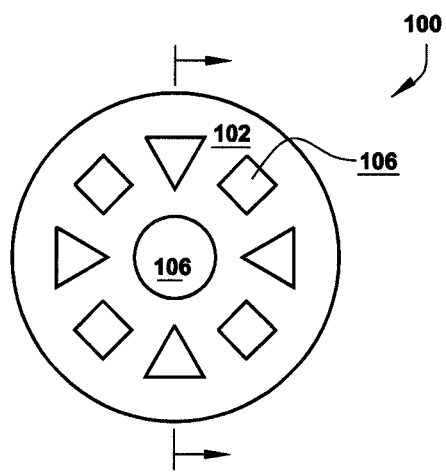
FIG. 8 is a top plan view of another first member 100 in keeping with one embodiment of the present invention wherein the protrusions 106 and the receiving zones 206 are a combination of triangle and diamond shapes.
Figure 9:
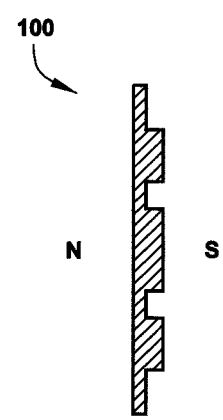
FIG. 9 is a cross-sectional view of the first member 100 of FIG. 8 taken along centerline thereof.
Figure 10:
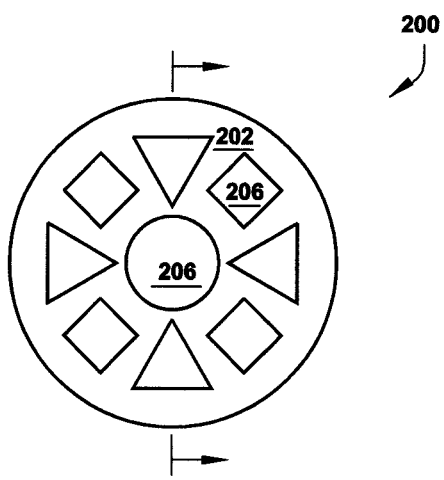
FIG. 10 is a top plan view of a second member 200 configured to align with the first member 100 of FIG. 8.
Figure 11:
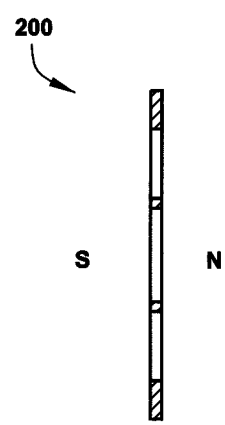
FIG. 11 is a cross-sectional view of the second member 200 of FIG. 10 taken along centerline thereof.
Figure 12:
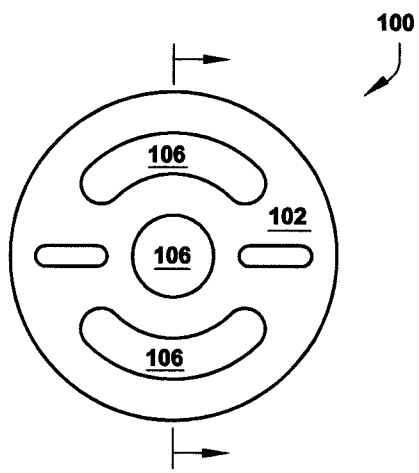
FIG. 12 is a top plan view of another first member 100 in keeping with one embodiment of the present invention wherein the protrusions 106 and the receiving zones 206 are a combination of circumferential and radial shapes.
Figure 13:
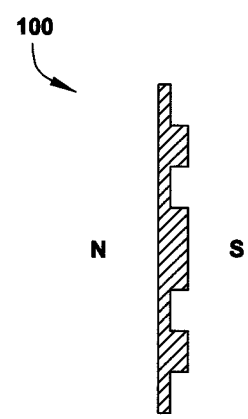
FIG. 13 is a cross-sectional view of the first member 100 of FIG. 12 taken along centerline thereof.
Figure 14:
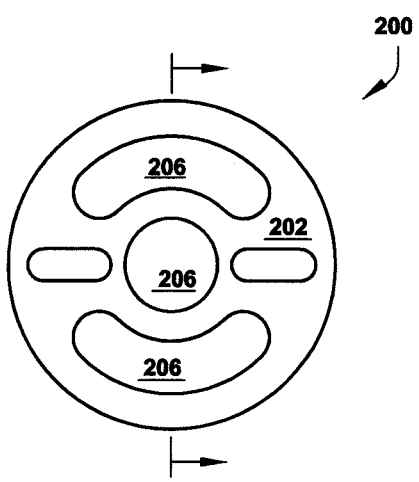
FIG. 14 is a top plan view of a second member 200 configured to align with the first member 100 of FIG. 12.
Figure 15:
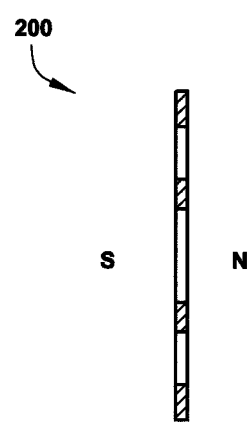
FIG. 15 is a cross-sectional view of the second member 200 of FIG. 14 taken along centerline thereof.
Figure 16:
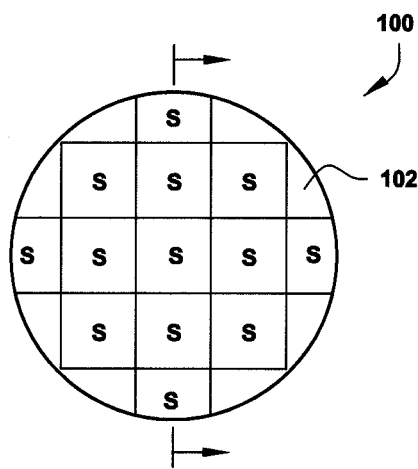
FIG. 16 is a top plan view of another first member 100 in keeping with one embodiment of the present invention wherein the receiving zones 206 are recessions that do not continue through the entire thickness of the second member 200 and, as just one example of such an embodiment, form a checkerboard of recessions for aligning with a matching checkerboard of protrusions 106 on the mating surface 102 of the first member 100.
Figure 17:
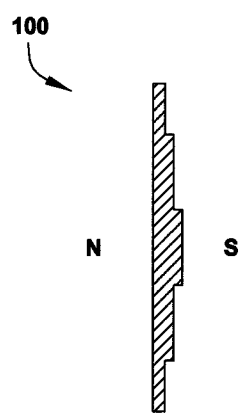
FIG. 17 is a cross-sectional view of the first member 100 of FIG. 16 taken along centerline thereof.
Figure 18:
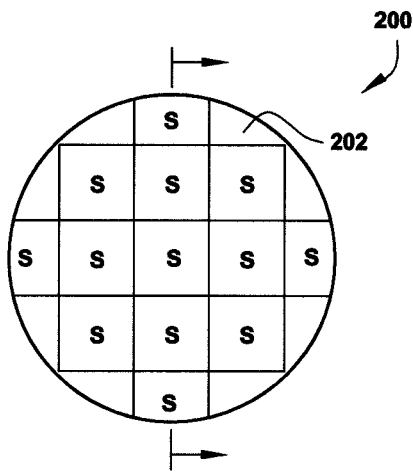
FIG. 18 is a top plan view of a second member 200 configured to align with the first member 100 of FIG. 16.
Figure 19:
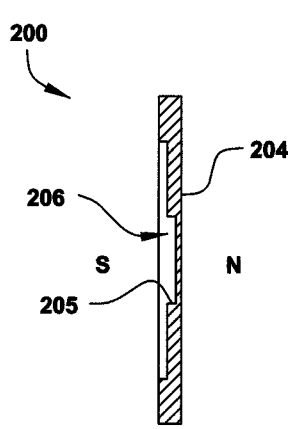
FIG. 19 is a cross-sectional view of the second member 200 of FIG. 18 taken along centerline thereof.
Figure 20:
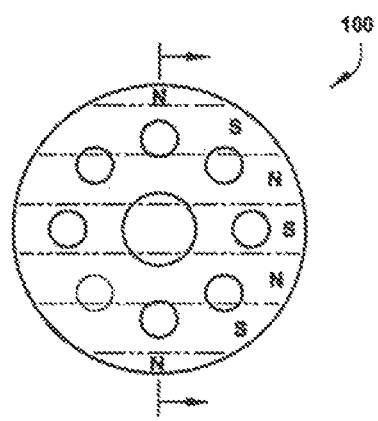
FIG. 20 is a top plan view of another first member 100 in keeping with one embodiment of the present invention wherein the magnetic pattern imposed thereon is non-homogeneous.
Figure 21:
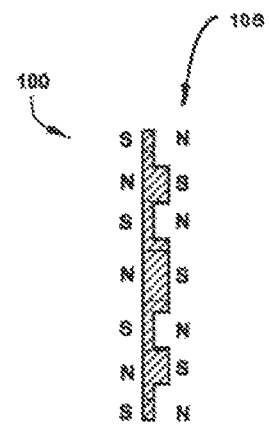
FIG. 21 is a cross-sectional view of the first member 100 of FIG. 20 taken along centerline thereof.
Figure 22:
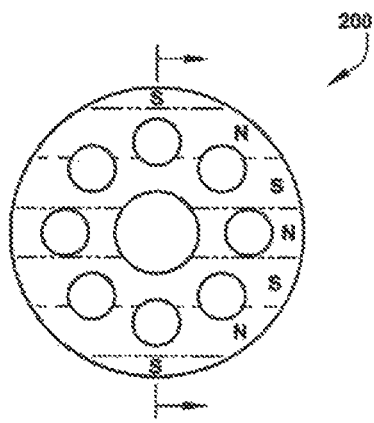
FIG. 22 is a top plan view of a second member 200 configured to align with the first member 100 of FIG. 20.
Figure 23:
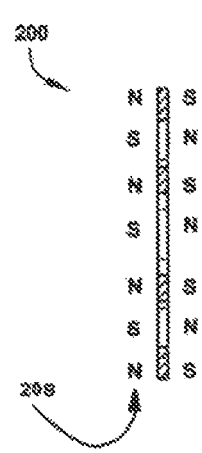
FIG. 23 is a cross-sectional view of the second member 200 of FIG. 22 taken along centerline thereof.
Figure 24:
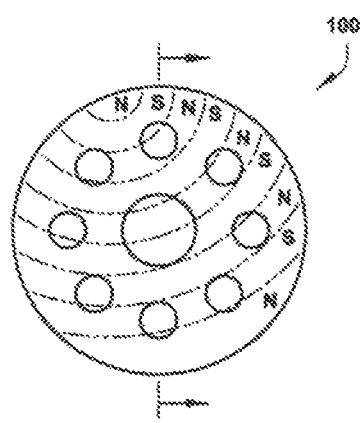
FIG. 24 is a top plan view of another first member 100 in keeping with one embodiment of the present invention wherein the magnetic pattern imposed thereon is a different non-homogeneous pattern.
Figure 25:
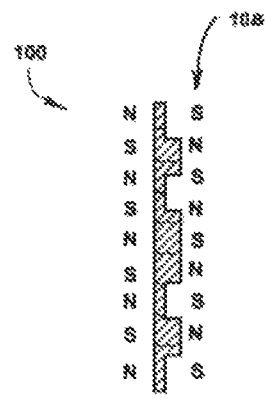
FIG. 25 is a cross-sectional view of the first member 100 of FIG. 24 taken along centerline thereof.
Figure 26:
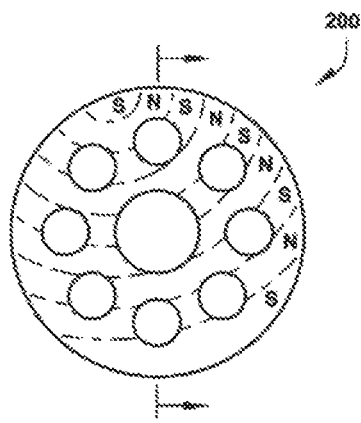
FIG. 26 is a top plan view of a second member 200 configured to align with the first member 100 of FIG. 24.
Figure 27:
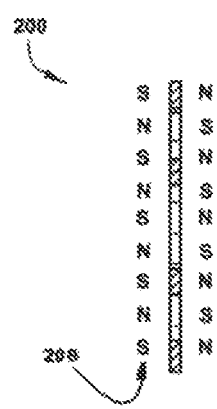
FIG. 27 is a cross-sectional view of the second member 200 of FIG. 26 taken along centerline thereof.
Figure 28:
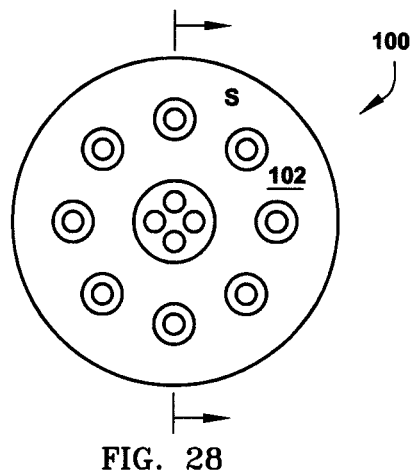
FIG. 28 is a top plan view of another first member 100 in keeping with another embodiment of the present invention wherein there are more than two separate layers.
Figure 29:
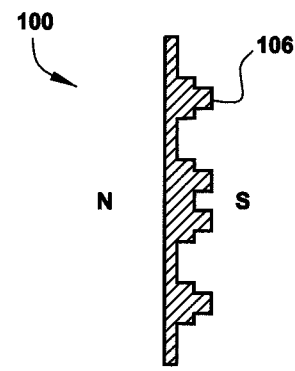
FIG. 29 is a cross-sectional view of the first member 100 of FIG. 28 taken along centerline thereof.
Figure 30:
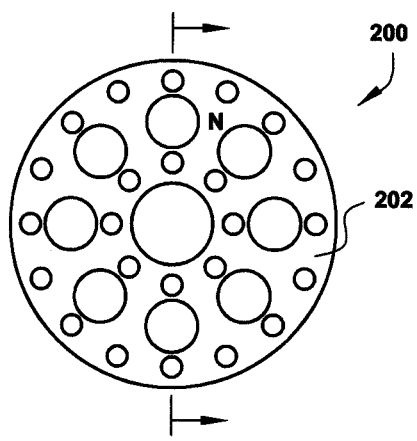
FIG. 30 is a top plan view of a second member 200 configured to align with the first member 100 of FIG. 28 and further having protrusions to align with further members.

In some embodiments, the first and second members 100 and 200 may be separated by a non-magnetic material 400, such as an elastomer, adhesive, or the like, as shown in FIG. 3. This non-magnetic material 400 may be used to help maintain the two members 100 and 200 in proper relationship, reduce wear and tear, and/or maintain members 100 and 200 at a predetermined range of distance between one another in order to modulate the magnetic flux lines at the application surface.

Example 2

FIGS. 8 through 11 show another embodiment of the present invention wherein the protrusions 106 and the receiving zones 206 are a combination of triangle and diamond shapes. Additionally, although the device 50 of FIGS. 1 through 7 and 8 through 11 are illustrated as circular, the device 50 could just as easily be configured into any shape. In fact, triangular, square, and hexagonal shaped devices could better cover a two-dimensional region, such as a pad, blanket, insole, or the like. Such other shapes are fully and equally contemplated as alternative embodiments within the present invention.

Example 3

Similarly, shown in FIGS. 12 through 15 is another embodiment of the present invention wherein the protrusions 106 and the receiving zones 206 are a combination of circumferential and radial shapes, and shown in FIGS. 16 through 19, is still a further embodiment of the present invention wherein the receiving zones 206 are recessions that do not continue through the entire thickness of the second member 200 and, as just one example of such an embodiment, form a checkerboard of recessions for aligning with a matching checkerboard of protrusions 106 on the mating surface 102 of the first member 100.

Examples 4 and 5

Although the members 100 and 200 of the embodiments discussed so far have been illustrated as having generally homogeneous magnetic patters, as shown in FIGS. 20 through 28, other embodiments of the present invention may include any number of other non-homogeneous patterns imposed on the first and second members 100 and 200, provided that at least some portion of the magnetic pattern 108 on the first member encounters a portion of the magnetic pattern 208 on the second member 200 in such a way that a repulsive magnetic force is exerted between the two layers.

Example 6

In some embodiments, there may be further members or layers, in which the second member 200, or even the first member 100, may similarly align with the additional layer or layers that exhibit similarly opposing magnetic patterns 108 and 208, each layer comprising protrusions and/or receiving zones that may facilitate the above-mentioned alignment and engage in magnetic communication with other layers so as to product a repulsive force and/or a plurality of magnetic flux lines at an application surface of the device 50.

Figure 31:
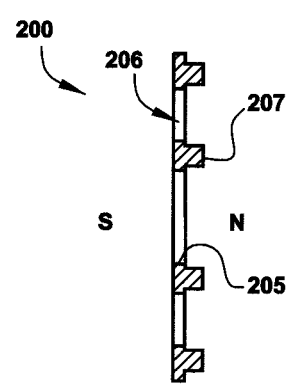
FIG. 31 is a cross-sectional view of the second member 200 of FIG. 30 taken along centerline thereof.
Figure 32:
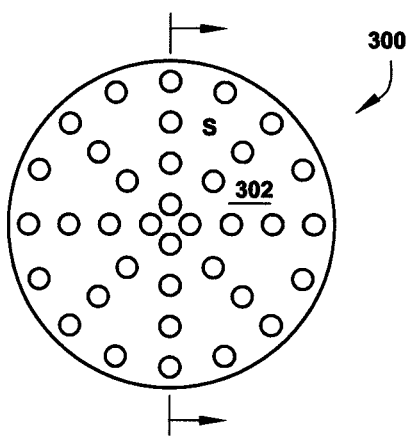
FIG. 32 is a top plan view of a third member 300 configured to align with the first member 100 of FIG. 28 and/or the second member 200 of FIG. 30.
Figure 33:
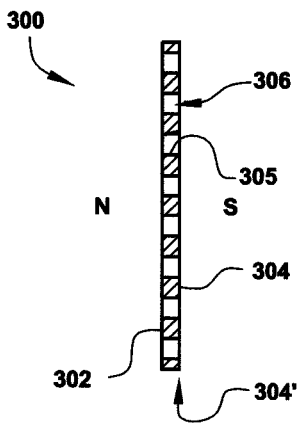
FIG. 33 is a cross-sectional view of the third member 300 of FIG. 32 taken along centerline thereof.

Thus, FIGS. 29 through 33 illustrate just one example in keeping with the present invention in which more than two layers are aligned. As illustrated in FIG. 32, the second member, in addition to having receiving zones 206 for receiving protrusions 106 from the first member 100, may also have protrusions 207. These protrusions 207 may then be received by receiving zones 306 of a third member 300. Indeed, or alternatively, the protrusions 106 of the first member 100 may extend be received by receiving zones 306 of a third member 300 as illustrated in FIG. 31.

As a result, magnetic repulsion of faces 102 and 202 forces the first member 100 and second member 200 apart and magnetic repulsion of faces 204 and 302 force the second member 200 and third member 300 apart, and so on (not shown). Combined, the multi-layered magnetic device exhibits a dynamic plurality of magnetic flux lines at an application surface 304' when the layers are pressed together and then released, as discussed above.

While the present invention has been described with regards to particular embodiments, it is recognized that additional variations of the present invention may be devised without departing from the inventive concept.

What is claimed is:

1. A multi-layer magnetic therapeutic device for use on a mammal comprising
   a first sheet having a first mating face that has a plurality of protrusions, and
   a second sheet having a second mating face that has one or more internal edges that define a plurality of receiving zones for pairing with the plurality of protrusions of the first mating face and an application surface opposite the second mating face,
   wherein at least a portion of the first mating face has a first magnetic pattern, wherein at least a portion of the second mating face has a second magnetic pattern, wherein the protrusions of the first mating face are configured to be received in the receiving zones of the second mating face, wherein at least one region of the first mating face faces at least one region of the second mating face, creating a repulsive force between the first and second mating faces, and wherein the first and second magnetic patterns are configured to produce magnetic flux lines at the application surface that vary in time as the distance between the first and second sheets varies in time, wherein the first and second magnetic patterns are configured to therapeutically treat the mammal by applying the magnetic flux lines.

2. A device as in claim 1 wherein the first magnetic pattern extends across at least one protrusion of the plurality of protrusions.

3. A device as in claim 1 wherein there are two or more protrusions and two or more receiving zones configured so that, when the protrusions are received in the receiving zones, the first sheet is fixed relative to the second sheet in a plane generally parallel to a plane defined by the second mating face.

4. A device as in claim 1 wherein the protrusions loosely fit within the receiving zones such that the receiving zones can move in a direction generally perpendicular to the second mating face.

5. A device as in claim 1 wherein the protrusions loosely fit within the receiving zones such that the protrusions can move in the receiving zones.

6. A device as in claim 5 wherein the movement of the protrusions in the receiving zones is in a direction generally perpendicular to the second mating face.

7. A device for therapeutic use on a mammal, comprising:
a first member having a plurality of protrusions, and
a second member defining an application surface and having a plurality of receiving zones for aligning with the plurality of protrusions of the first member,
wherein at least a portion of the first member has a first magnetic pattern, wherein at least a portion of the second member has a second magnetic pattern, wherein the protrusions are aligned with the receiving zones, wherein at least one region of the first member faces at least one region of the second member forcing together magnetic patterns of like polarity on the first member facing region and the second member facing region, wherein the first member and the second member are configured to magnetically repulse one another and to produce a plurality of magnetic flux lines at the application surface that vary in time as the distance between the first and second sheets varies in time wherein the first and second magnetic patterns are configured to therapeutically treat the mammal by applying the magnetic flux lines.

8. A device as in claim 7 wherein the first magnetic pattern extends across at least one protrusion of the plurality of protrusions.

9. A device as in claim 7 wherein there are two or more protrusions and two or more receiving zones configured so that when the protrusions are received in the receiving zones, the first sheet is fixed relative to the second member in a plane generally parallel to a plane defined by the second member.

10. A device as in claim 7 wherein the protrusions loosely fit within the receiving zones such that the receiving zones can move in a direction generally perpendicular to the second member.

11. A device as in claim 7 wherein the protrusions loosely fit within the receiving zones such that the protrusions can move in the receiving zones.

12. A device as in claim 11 wherein the movement of the protrusions in the receiving zones is a direction generally perpendicular to the second member.

13. A multi-layer magnetic therapeutic device for use on a mammal comprising
a first sheet having a first mating face that has a plurality of protrusions, and
a second sheet having a second mating face that has one or more internal edges that define a plurality of receiving zones for pairing with the plurality of protrusions of the first mating face and defining an application surface opposite the second mating face,
wherein at least a portion of the first mating face has a first magnetic pattern and wherein at least a portion of the second mating face has a second magnetic pattern, wherein the protrusions of the first mating face are configured to match with the receiving zones of the second mating face, at least one region of the first mating face faces at least one region of the second mating face, wherein the matching of the first mating face and the second mating face creates a repulsive force between the first and second mating faces
wherein two or more protrusions of the plurality of protrusions fit within two or more receiving zones of the plurality of receiving zones, wherein the two or more protrusions are received in the two or more receiving zones, wherein the two or more receiving zones can move in a direction generally perpendicular to the second mating face and fixed relative to the second sheet in a plane generally parallel to a plane defined by the second mating face, and the first and second magnetic patterns are configured to produce a plurality of magnetic flux lines that varies in time as the distance between the first and second sheets varies in time, wherein the first and second patterns are configured to have a therapeutic effect on the mammal being treated by applying the magnetic flux lines, and
wherein the first magnetic pattern extends across at least one protrusion of the plurality of protrusions.

* * * * *